(12) United States Patent
Sayeg et al.

(10) Patent No.: US 7,951,077 B2
(45) Date of Patent: May 31, 2011

(54) METHOD AND INSTRUMENTS FOR BREAST AUGMENTATION MAMMAPLASTY

(76) Inventors: Ayoub Sayeg, West Bloomfield, MI (US); John E. Nemazi, Bloomfield Hills, MI (US)

( * ) Notice: Subject to any disclaimer, the term of this patent is extended or adjusted under 35 U.S.C. 154(b) by 1291 days.

(21) Appl. No.: 11/182,995

(22) Filed: Jul. 15, 2005

(65) Prior Publication Data

US 2007/0021655 A1  Jan. 25, 2007

(51) Int. Cl.
  *A61B 1/32* (2006.01)
(52) U.S. Cl. ........ 600/210; 600/201; 600/204; 600/212; 600/215; 600/235
(58) Field of Classification Search .......... 600/201, 600/204, 208, 214, 218–220, 222, 232, 233, 600/210–212, 215, 235
See application file for complete search history.

(56) References Cited

U.S. PATENT DOCUMENTS

| | | | | |
|---|---|---|---|---|
| 4,226,228 A | | 10/1980 | Shin et al. | |
| 4,337,763 A | * | 7/1982 | Petrassevich | 600/210 |
| 4,570,614 A | * | 2/1986 | Bauman | 600/195 |
| 5,035,232 A | * | 7/1991 | Lutze et al. | 600/213 |
| 5,230,621 A | * | 7/1993 | Jacoby | 433/29 |
| 5,258,026 A | | 11/1993 | Johnson et al. | |
| 5,318,010 A | * | 6/1994 | Lundberg | 600/222 |
| 5,328,365 A | * | 7/1994 | Jacoby | 433/29 |
| 5,339,801 A | * | 8/1994 | Poloyko et al. | 600/214 |
| 5,431,153 A | * | 7/1995 | Lee | 600/183 |
| 5,490,819 A | * | 2/1996 | Nicholas et al. | 600/201 |
| 5,500,019 A | | 3/1996 | Johnson et al. | |
| 5,584,796 A | | 12/1996 | Cohen | |
| 5,667,472 A | * | 9/1997 | Finn et al. | 600/104 |
| 5,667,473 A | * | 9/1997 | Finn et al. | 600/104 |
| 5,667,480 A | * | 9/1997 | Knight et al. | 600/210 |
| 5,722,934 A | * | 3/1998 | Knight et al. | 600/201 |
| 5,725,479 A | * | 3/1998 | Knight et al. | 600/210 |
| 5,817,005 A | | 10/1998 | Cohen | |
| 5,846,192 A | * | 12/1998 | Teixido | 600/210 |
| 5,882,298 A | * | 3/1999 | Sharratt | 600/213 |
| 5,902,315 A | * | 5/1999 | DuBois | 606/190 |
| 5,922,004 A | * | 7/1999 | DuBois | 606/190 |
| 5,928,135 A | * | 7/1999 | Knight et al. | 600/104 |
| 5,928,138 A | * | 7/1999 | Knight et al. | 600/201 |
| 6,099,547 A | * | 8/2000 | Gellman et al. | 606/198 |
| 6,129,661 A | * | 10/2000 | Iafrati et al. | 600/121 |
| 6,139,489 A | * | 10/2000 | Wampler et al. | 600/109 |
| 6,193,653 B1 | * | 2/2001 | Evans et al. | 600/210 |
| 6,196,968 B1 | * | 3/2001 | Rydin et al. | 600/210 |

(Continued)

OTHER PUBLICATIONS

Internet Archive WayBack Machine, Search for www.flalife.com.*

(Continued)

*Primary Examiner* — Eduardo C Robert
*Assistant Examiner* — Ellen C Hammond
(74) *Attorney, Agent, or Firm* — Brooks Kushman P.C.

(57) ABSTRACT

A method and instruments for performing breast augmentation mammaplasty in a patient are provided. The method includes making an incision to gain access to an area underneath the breast of the patient, and providing a retractor including a shaft and a tubular member connected to the shaft. The tubular member includes a hollow endoscope guide portion and a generally flattened blade portion, where the endoscope guide portion transitions into the blade portion such that an end of the blade extends beyond an end of the endoscope guide. The method further includes inserting the retractor at least partially through the incision to aid in placing a breast implant within the patient.

23 Claims, 5 Drawing Sheets

U.S. PATENT DOCUMENTS

| | | | | |
|---|---|---|---|---|
| 6,206,823 B1* | 3/2001 | Kolata et al. | ............... | 600/129 |
| 6,228,025 B1* | 5/2001 | Hipps et al. | ............... | 600/213 |
| 6,322,499 B1* | 11/2001 | Evans et al. | ............... | 600/212 |
| 6,350,236 B1* | 2/2002 | Hipps et al. | ............... | 600/213 |
| 6,413,208 B1* | 7/2002 | Schollhorn et al. | ............... | 600/164 |
| 6,428,474 B1* | 8/2002 | Weiss | ............... | 600/224 |
| 6,468,206 B1* | 10/2002 | Hipps et al. | ............... | 600/213 |
| 6,482,153 B1* | 11/2002 | Hipps et al. | ............... | 600/213 |
| 6,554,768 B1* | 4/2003 | Leonard | ............... | 600/213 |
| 6,585,727 B1* | 7/2003 | Cashman et al. | ............... | 606/16 |
| 6,592,582 B2* | 7/2003 | Hess et al. | ............... | 606/49 |
| 6,592,604 B2* | 7/2003 | Hess et al. | ............... | 606/190 |
| 6,648,815 B2* | 11/2003 | Schoellhorn et al. | ............... | 600/164 |
| 6,656,176 B2* | 12/2003 | Hess et al. | ............... | 606/51 |
| 6,740,102 B2* | 5/2004 | Hess et al. | ............... | 606/159 |
| 6,805,666 B2* | 10/2004 | Holland et al. | ............... | 600/212 |
| 6,817,978 B2* | 11/2004 | Holland et al. | ............... | 600/212 |
| 6,951,538 B2* | 10/2005 | Ritland | ............... | 600/210 |
| 7,306,559 B2* | 12/2007 | Williams | ............... | 600/245 |
| 7,314,479 B2* | 1/2008 | Wellman et al. | ............... | 606/205 |
| 2005/0085699 A1* | 4/2005 | Weiss | ............... | 600/221 |

OTHER PUBLICATIONS

Fiber Lighted Retractors. http://web.archive.org/web/20041111000048/flalife.com/fiberretractors.htm.*

W.S. Ho, Endoscopic-assisted subcutaneous mastectomy and axillary dissection with immediate mammary prosthesis reconstruction for early breast cancer, 2002, Surg Endosc, 16: 302-306.*

Internet Archive WayBack Machine, Aug. 2009, Search for www.flalife.com.*

Fiber Lighted Retractors. Feb. 2004, http://web.archive.org/web/20041111000048/flalife.com/fiberretractors.htm.* www.snowdenpencer.com. Emory EndoPlastic™ Retractor, Jun. 2005.

William R. Burden et al., Endoscopic Breast Subpectoral Augmentation for Second-Degree Breast Ptosis, Annals of Plastic Surgery, vol. 46, No. 3, Mar. 2001, pp. 238-241.

Richard Dowden, M.D., Keeping the Transumbilical Breast Augmentation Procedure Safe, Plastic and Reconstructive Surgery, vol. 108, No. 5, Oct. 2001, pp. 1389-1400.

Ruth Maria Graf et al., Subfascial Breast Implant: A New Procedure, Plastic and Reconstructive Surgery, vol. 111, No. 2, Feb. 2003, pp. 904-908.

Richard Dowden, M.D., Dispelling the Myths and Misconceptions about Transumbilical Breast Augmentation, Plastic and Reconstructive Surgery, vol. 106, No. 1, Jul. 2000, pp. 190-194.

* cited by examiner

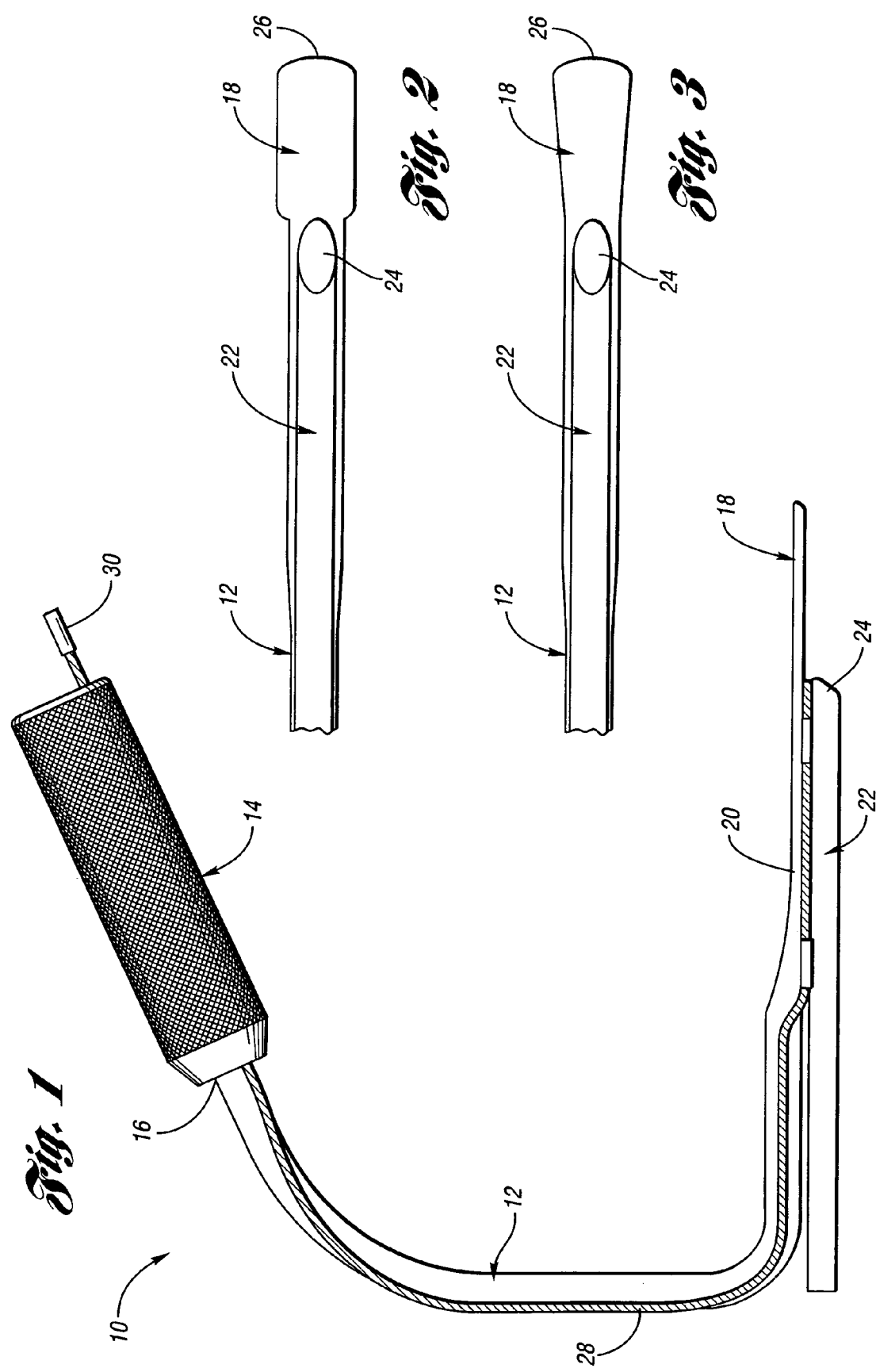

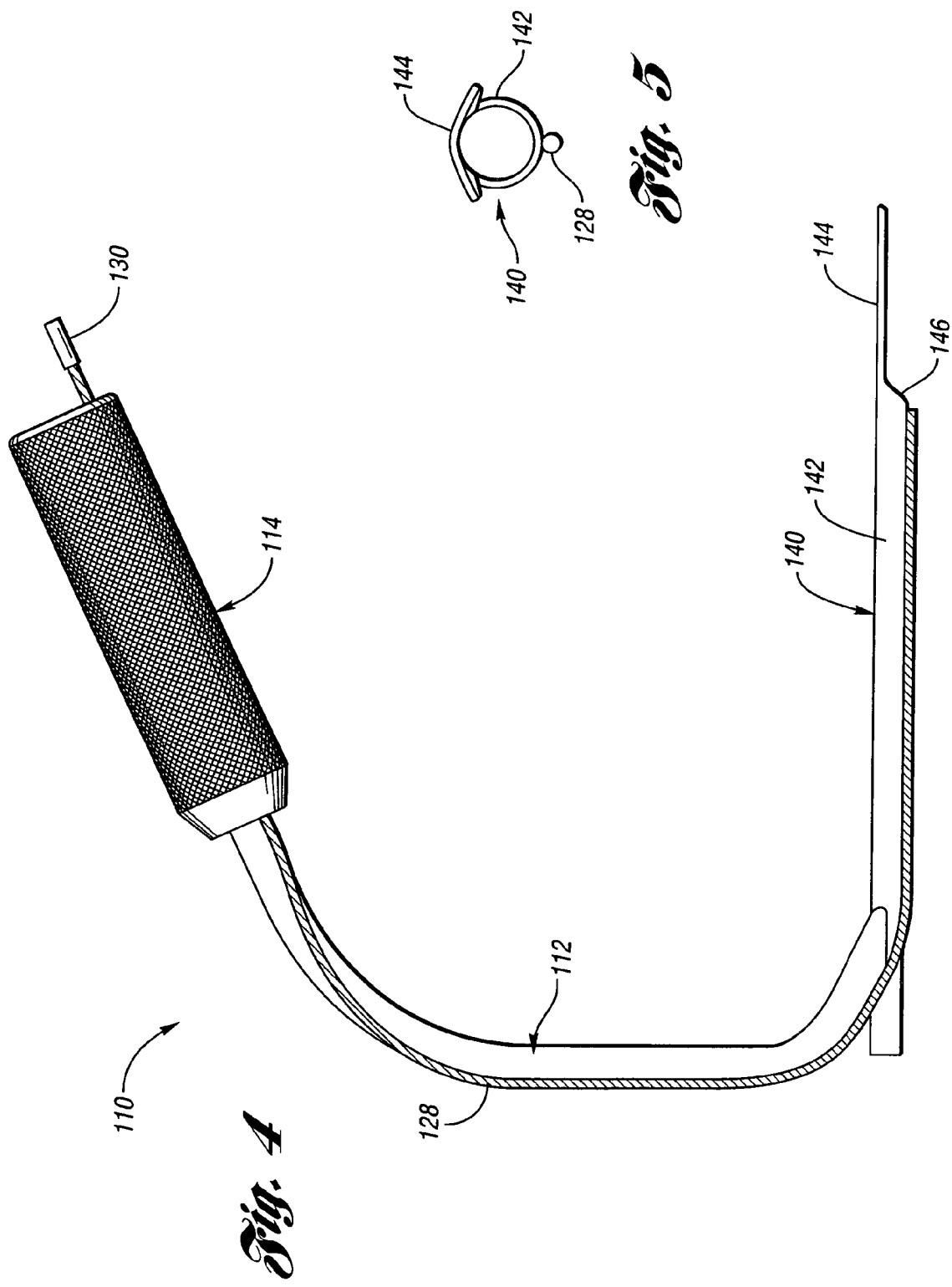

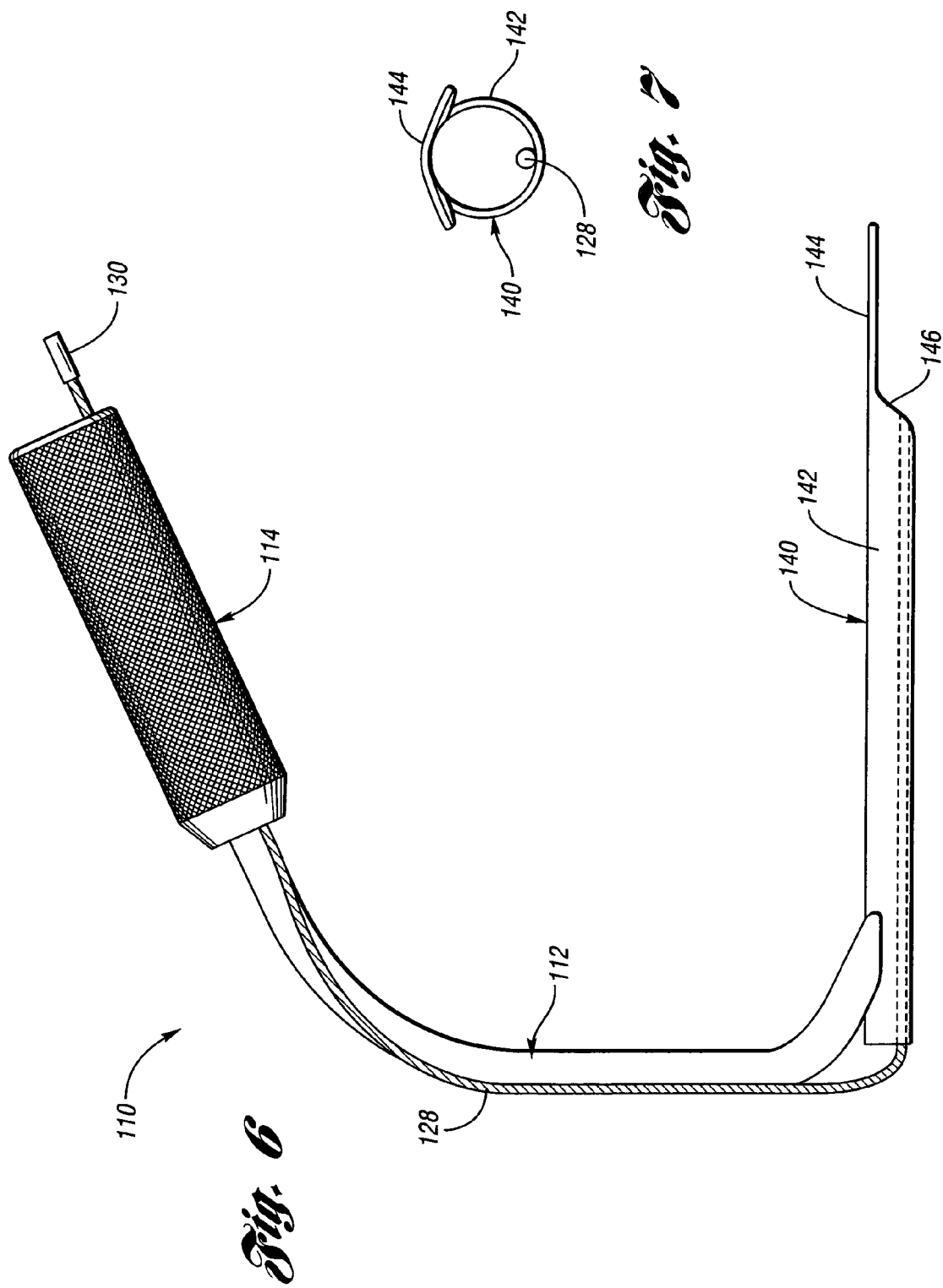

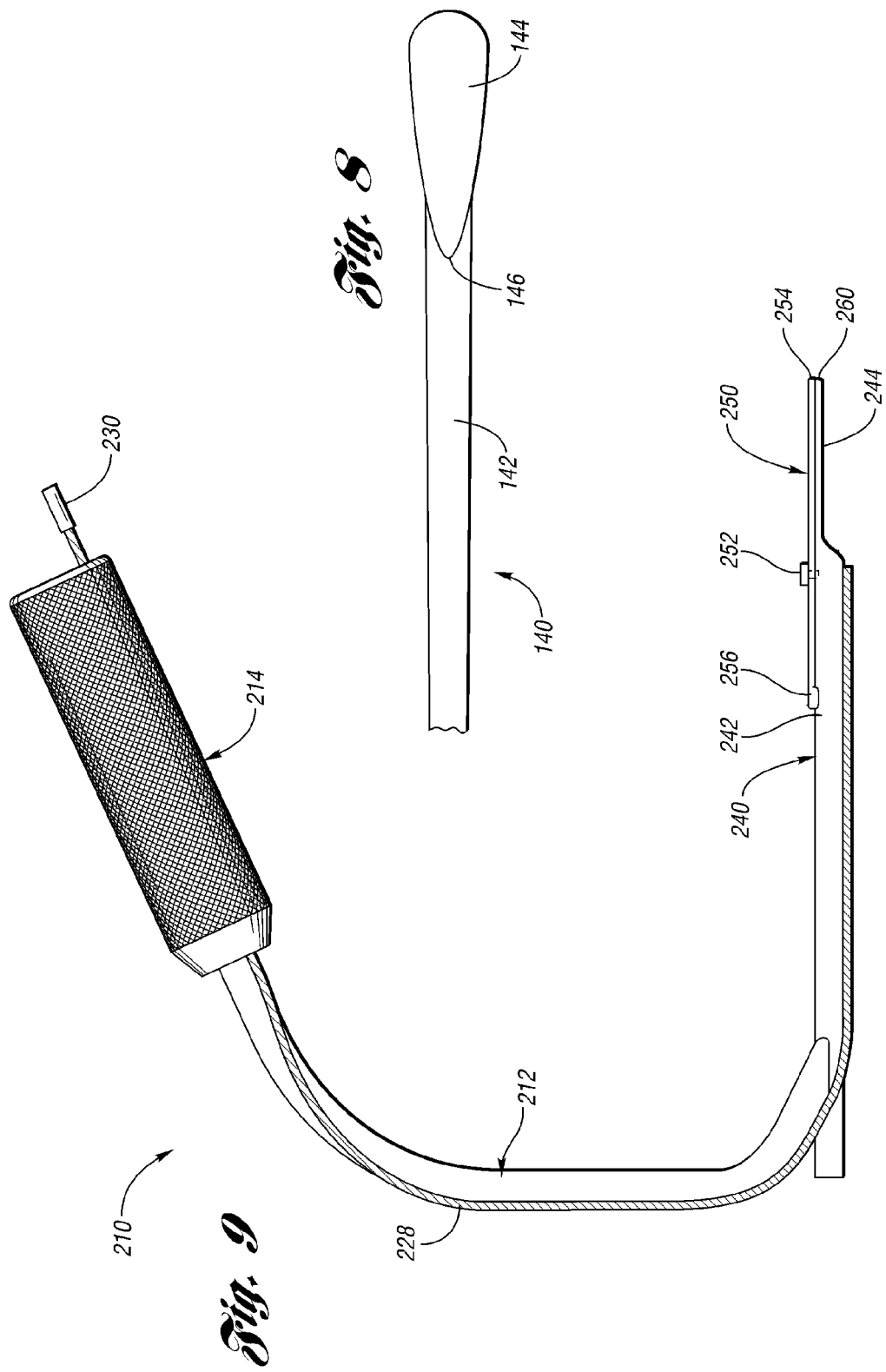

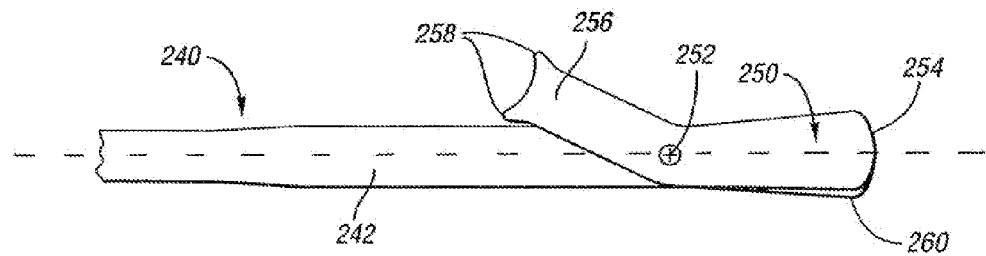
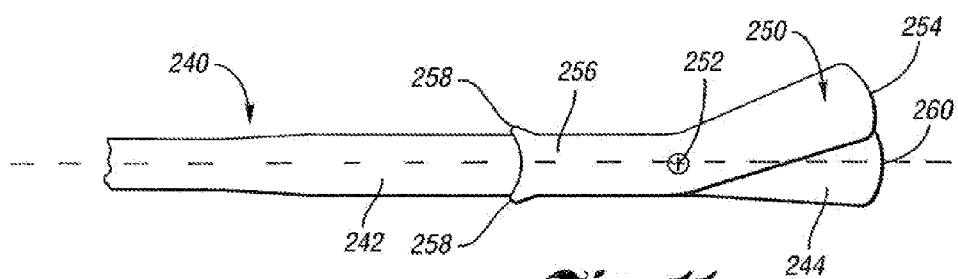
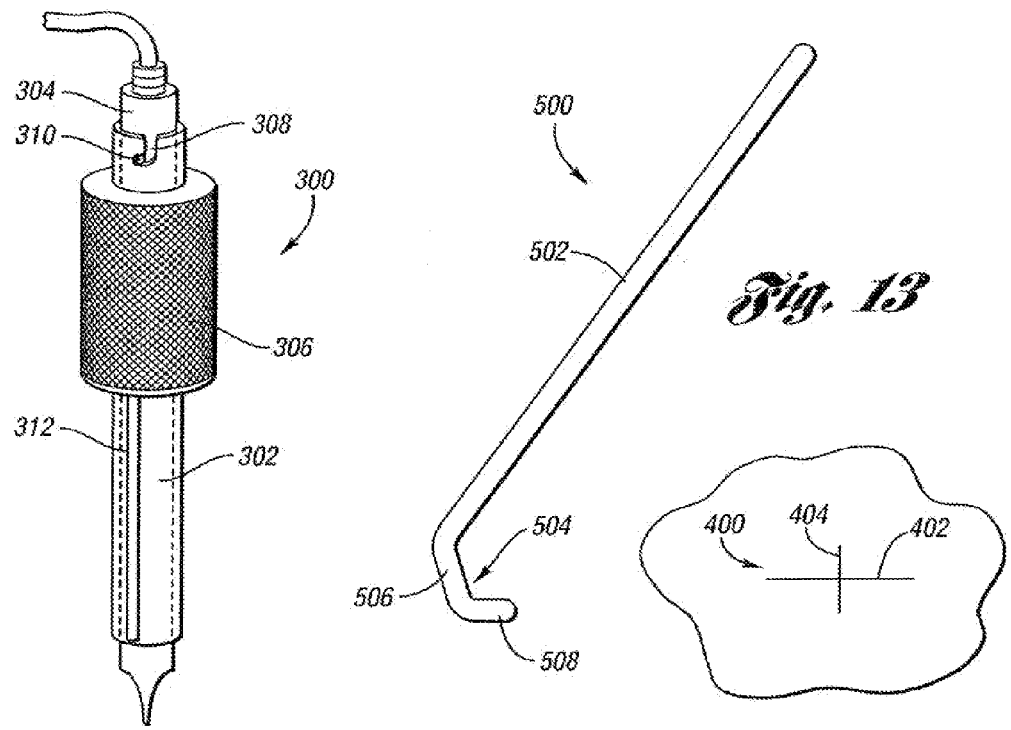

METHOD AND INSTRUMENTS FOR BREAST AUGMENTATION MAMMAPLASTY

BACKGROUND OF THE INVENTION

1. Field of the Invention

This invention relates to a method and instruments for breast augmentation mammaplasty, as well as other endoscopic surgical procedures.

2. Background Art

Breast augmentation is a surgical procedure that has been performed for many years. Current methods of breast augmentation involve the placement of an implant beneath each breast, either on top of or beneath the pectoralis major muscle underlying the breast. Insertion of the implant can be accomplished using several different incision sites, including transaxillary (armpit), periumbilical (navel), and inframammary (crease). The inframammary incision is the most common incision for placement of a breast implant, as it allows the surgeon to work in close proximity to the breast, thus allowing greater control over implant placement, and typically requires the least operative duration. Furthermore, almost all revision surgeries, should they be necessary, can be performed via this incision. However, the inframammary approach currently requires a 3 to 4 cm incision in order to dissect a subpectoral pocket and insert the breast implant, which can result in an undesirable scar on the anterior surface of the breast.

BRIEF DESCRIPTION OF THE DRAWINGS

FIG. 1 is a side elevational view of a retractor for use in breast augmentation mammaplasty according to one aspect of the present invention;

FIG. 2 is a partial, bottom plan view of one embodiment of the retractor blade and endoscope guide of a retractor as shown in FIG. 1;

FIG. 3 is a partial, bottom plan view of another embodiment of the retractor blade and endoscope guide of a retractor as shown in FIG. 1;

FIG. 4 is a side elevational view of a retractor having a combined endoscope guide and blade according to another aspect of the present invention;

FIG. 5 is an end elevational view of the retractor of FIG. 4;

FIG. 6 is a side elevational view of an alternative embodiment of a retractor having a combined endoscope guide and blade;

FIG. 7 is an end elevational view of the retractor of FIG. 6;

FIG. 8 is a partial bottom plan view of the retractor shown in FIG. 6;

FIG. 9 is a side elevational view of a retractor having an secondary blade in accordance with another aspect of the present invention;

FIG. 10 is a partial top plan view of the retractor of FIG. 9 with the secondary blade in a closed position;

FIG. 11 is a partial top plan view of the retractor of FIG. 9 with the secondary blade in an open position;

FIG. 12 is a front elevational view of a guide for use in electrocautery dissection according to the present invention;

FIG. 13 is a side elevational view of an additional retractor which can be utilized in accordance with the present invention; and FIG. 14 is a schematic illustration of an incision used for placement of the breast implant according to the method of the present invention; and

DETAILED DESCRIPTION OF THE INVENTION

As required, detailed embodiments of the present invention are disclosed herein; however, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for the claims and/or as a representative basis for teaching one skilled in the art to variously employ the present invention.

Turning first to FIGS. 1-3, an endoscopic retractor in accordance with the present invention is illustrated and designated generally by reference numeral 10. As is known in the art, an endoscopic retractor is a hand-held, rod-like structure which can be used to simultaneously retract and view body tissues, such as during a breast augmentation mammaplasty procedure. Retractor 10 is inserted into an incision in order to provide for tissue visualization and/or insertion of a breast implant, allowing the surgeon to provide traction and elevate body tissues using one hand, while leaving the surgeon's other hand free for dissection.

Retractor 10 includes a shaft 12, a handle 14 attached to shaft 12 at a first end 16 thereof, and a blade 18 which may be integrally formed with shaft 12 at a second end 20 thereof. Shaft 12 may be curved and have a generally circular cross-section as shown herein, although other shapes of shaft 12 are fully contemplated in accordance with the present invention. Handle 14 may also be circular in cross-section, and can include a surface which is knurled or otherwise constructed to facilitate easy gripping by the surgeon.

With reference again to FIG. 1, retractor 10 further includes a hollow endoscope guide 22 for permanently or removably receiving an endoscope or other devices (not shown). Guide 22 may be mounted to shaft 12, such as via soldering, welding, or an adhesive. Alternatively, guide 22 may be mechanically connected to retractor 10 with screws, clamps, or the like. Guide 22 is configured to receive and hold an endoscope or other devices in position under blade 18, where blade 18 may extend beyond the end 24 of guide 22 as depicted in FIGS. 1-3. According to one aspect of the present invention, blade 18 may extend about 2.0 cm beyond the end 24 of guide 22. In one embodiment, guide end 24 may be constructed to have an angle, such as of approximately 30°, to allow an increased field of vision of the endoscope. In accordance with the present invention, guide 22 may have a diameter sufficient to receive a standard 10 mm endoscope, or could be of smaller size for receiving a standard 5 mm endoscope. Of course, other sizes of guide 22 are also fully contemplated.

As best shown in the bottom plan views of FIGS. 2 and 3, blade 18 may be configured to be generally flattened, and may include a rounded end 26 which, according to one aspect of the present invention, can have a width of between about 1.2 cm and 1.6 cm. It is understood that the term "generally flattened" as used herein may encompass blade cross-sections which are generally arcuate as well as blade shapes which have a more rectangular cross-section, but that blade 18 is not limited to these configurations. Blade 18 can taper in width from blade end 26 to guide end 24, wherein the width of blade 18 near guide end 24 may be between about 0.8 cm and 1.2 cm. Of course, blade 18 is not limited to these dimensions. The blade taper can be in the form of a shoulder, as in FIG. 2, or a gradual taper from blade end 26 to guide end 24 as depicted in FIG. 3. This taper of blade 18 may provide for easier insertion through small incisions, allowing the surgeon to minimize the length of the incision required for surgery.

As is known in the art, an endoscope is an imaging device which can be used to observe the body tissues exposed during surgery. An endoscope is configured to generate electrical signals which can be processed to form image or video signals for display on a display device via either a wireline or wireless connection. An endoscope utilized in conjunction with retractor 10 of the present invention may also include a light for illuminating the body tissues. As shown in FIG. 1, retractor 10 can be provided with one or more passages 28 for suction, such as for the evacuation of smoke resulting from electrocautery dissection, for irrigation, or both. This passage 28 may be affixed along shaft 12 and blade 18 exterior to guide 22 as shown, or alternatively could be configured to run within guide 22 (see, for example, FIGS. 6-7). A fitting 30 may be provided, such as near handle 14, for connection of passage 28 to a vacuum and/or irrigation source.

While a generally U-shaped retractor 10 is shown and described herein, it is understood that retractor 10 according to the present invention can have other shapes, such as a J-shape or a shape where blade 18 and handle 14 are disposed at right angles with respect to one another. The overall length of retractor 10 will vary with the intended use and is not limited to any particular dimensions, but may generally be about 12 to 24 inches in length measured from end to end.

According to the present invention, retractor 10 may be constructed from a rigid metallic material such as stainless steel or titanium, but may alternatively be made from other materials such as plastic, rubber, or another material suitable for surgical use. Retractor 10 may be designed to be sterilizable, such as in an autoclave or the like, and thus reusable, or alternatively may be designed to be disposable. In accordance with one aspect of the present invention, at least a portion of shaft 12, blade 18, and/or guide 22 are covered with an insulating material or constructed from a nonconductive material. Such a covering may protect tissue in contact with retractor 10 from exposure to electrical energy that could be discharged by an electrocautery device, electric scalpel, or other electrical device.

A retractor 110 in accordance with another aspect of the present invention is illustrated in FIGS. 4-8. Elements of retractor 110 that correspond with elements of retractor 10 are designated with similar reference numerals except for the addition of a "1" prefix, and the description of retractor 10 provided above may be applied to retractor 110 as appropriate.

Retractor 110 can include a handle 114 attached to shaft 112. Shaft 1112 may then be mounted via soldering, welding, adhesive, or mechanical means to a tubular member 140 having a hollow endoscope guide portion 142 and a generally flattened blade portion 144. Alternatively, shaft 112 could be hollow and integrally formed with tubular member 140, with a port (not shown) formed in shaft 112 for insertion of the endoscope. As shown in FIGS. 4-8, guide portion 142 smoothly transitions into blade portion 144, and retractor 110 eliminates soldered or other joints along guide portion 142 near blade portion 144. Blade portion 144 may have any width appropriate for the intended application, such as between about 1.2 cm and 1.6 cm, and may taper and extend beyond the end 146 of guide portion 142 as described above with reference to retractor 10. Guide portion 142 also can have any sizing, such as a diameter capable of receiving a standard 10 mm or 5 mm endoscope.

An endoscope or other device can be received within guide portion 142, and suction and/or irrigation can be provided via a passage 128 external to tubular member 140 as illustrated in FIGS. 4-5, or within tubular member 140 as shown in FIGS. 6-7. It is understood that tubular member 140 is not necessarily circular in cross-section, but can have any shape. For example, a generally oval shape of tubular member 140 may be desired in the embodiment depicted in FIGS. 6-7 wherein passage 128 is contained within tubular member 140.

The configuration of tubular member 140 may decrease the overall area of retractor 110 to be inserted through an incision as compared with separate endoscope guide and blade components, and thus may facilitate insertion and removal of retractor 110 through small incisions, allowing the surgeon to minimize the incision and potential scar resulting from a breast augmentation procedure. According to one aspect of the present invention, blade portion 144 may be as wide as possible for a desired incision length given the diameter of guide portion 142. In one example, the width of blade portion 144 may be about 1.4 to 1.8 times the diameter of guide portion 142. Of course, retractor 110 is not limited to this ratio of dimensions.

Still another retractor in accordance with the present invention is depicted in FIGS. 9-11 and designated generally by reference numeral 210. Elements of retractor 210 that correspond with elements of retractors 10 and 110 are designated with similar reference numerals, this time with the addition of a "2" prefix. Again, the description of retractors 10 and 110 provided above may be applied to retractor 210 as appropriate.

In this embodiment, retractor 210 includes a secondary blade 250 attached to tubular member 240 so as to be movable with respect thereto. According to one aspect of the present invention, secondary blade 250 is pivotably attached to tubular member 240 via a fastener 252, such as a pin, screw, projection, or the like. Secondary blade 250 could also be slidably connected or otherwise movably connected to tubular member 240. Like blade portion 244, secondary blade 250 may be generally flattened or have another shape. As best shown in FIGS. 10-11, secondary blade 250 has a first end 254 which may be generally rounded, and a second end 256 which may include a securing mechanism 258 for fixing the position of secondary blade 250 with respect to tubular member 240. The securing mechanism 258 can include flanges as shown to provide a snap or interference type fit around tubular member 240, or alternatively could include a detent, latch, or any other securing means between secondary blade 250 and tubular member 240. Secondary blade 250 can have any width as described previously for blade 18 and blade portion 144, and can have any length sufficient to allow manipulation of second end 256 while retractor 210 is inserted into the body.

When retractor 210 is to be inserted through an incision, securing mechanism 258 may be released such that secondary blade 250 is movable with respect to tubular member 240. Secondary blade 250 can then be pivoted such that first end 254 is generally aligned with and overlying an end 260 blade portion 244 in a closed position as depicted in FIG. 10, thus minimizing the width of retractor 210 for insertion. Once blade portion 244 and secondary blade 250 are positioned inside the body, secondary blade 250 may be rotated such that first end 254 is out of alignment with blade portion end 260 and into an open position as shown in FIG. 11, thereby increasing the total width of retractor 210. Secondary blade 250 may then be secured onto tubular member 240 to fix secondary blade 250 in this open position. When retractor 210 is to be removed from the body, securing mechanism 258 may again be detached from tubular member 240 and secondary blade 250 may be rotated back into alignment with blade portion 244 for easy manipulation and removal of retractor 210 through the incision.

Turning now to FIG. 12, a guide for an electrocautery device is depicted and designated generally with reference numeral 300. Guide 300 allows the use of an electrocautery or other electrical device while protecting skin and other soft tissues from inadvertent contact and potential injury. Guide 300 includes a tube 302 which may be constructed from a nonconductive material such as, but not limited to, plastic or the like. According to one aspect of the present invention, tube 302 may have a diameter of approximately 1.0 cm or smaller, large enough to accommodate an electrocautery device 304 while still able to easily pass through a small incision. Of course, other dimensions of tube 302 are also fully contemplated. Guide 300 can include a handle 306 at any location thereon, wherein handle 306 may be provided with a gripping surface. The length of guide 300 can vary according to the application and is not limited to any particular dimensions, but according to one aspect of the present invention may be approximately 4 inches.

In one embodiment, tube 302 and handle 306 can be integrally formed, and an electrocautery device 304 or other instrument can be received within tube 302 and secured thereto, such as via the groove 308 and projection 310 configuration depicted or by any other securing means. In another embodiment, electrocautery device 304 can be affixed within tube 302, and tube 302 can be removably received within and secured to handle 306. In either embodiment, electrocautery device 304 is secured within guide 300 for one-handed manipulation by the surgeon, and then can be quickly and easily unlocked and removed from guide 300 when necessary. Guide 300 may also include a light source, such as a fiberoptic light 312, to aid the surgeon in visualizing the tissues to be incised. Light 312 can be provided at any location on guide 300, such as the exterior mounting shown herein, or alternatively could be provided on the interior of guide 300. A battery and switch (not shown) could be included on guide 300, such as within handle 306, to allow the surgeon to selectively actuate light 312.

With reference to FIG. 13, an additional retractor 500 may be provided to assist the surgeon in holding back tissues during a surgical procedure. Retractor 500 includes a handle 502 and a blade 504, wherein blade 504 comprises a first segment 506 and a second segment 508. First segment 506 may be disposed at an angle with respect to handle 502 such as, but not limited to, between about 45° and 175°. Likewise, second segment 508 may be disposed at an angle with respect to first segment 506 such as, but not limited to, between about 25° to 135°. In addition, handle 502 as well as other parts of retractor 500 may be insulated to protect tissue in contact with retractor 500 from exposure to discharged electrical energy as described above. Furthermore, first segment 506, second segment 508, or both may contain a serrated portion (not shown) which may aid in gripping tissue. In one embodiment, handle 502 may have a length of approximately 4 inches, first segment 506 may have a length of approximately 1.5 cm, and second segment 508 may have a length of approximately 0.5 cm. Of course, retractor 500 is not limited to these dimensions.

A method for breast augmentation mammaplasty which utilizes the instruments according to the present invention will now be described. All procedures described herein are typically performed with the patient under general anesthesia.

To commence the surgery, an incision is made to gain access to an area underneath the breast. With reference to FIG. 14, according to one aspect of the present invention, the incision 400 may include a first segment 402 placed at or near the inframammary fold, or crease, of the breast, and then a second segment 404 may be placed generally in the middle of the first segment 402 and generally perpendicular thereto. The first segment 402 may be placed in a generally horizontal direction with the second segment 404 placed in a generally vertical direction, such that the resulting incision 400 somewhat resembles a "+" sign, wherein the incision 400 can be opened to more of a diamond-like shape having tissue flaps. In one embodiment, the first segment 402 may have a length of about 0.5 cm to 1.5 cm, and the second segment 404 may have a length of about 0.25 cm to 0.75 cm. Of course, the method of breast augmentation mammaplasty according to the present invention is not limited to this incision configuration or segment lengths.

A retractor, such as retractor 500 shown in FIG. 13, may be inserted at least partially through incision 400 and used to hold back body tissues in order to aid the surgeon in inserting other instruments. A retractor, such as any one of retractors 10, 110, 210 described above with reference to FIGS. 1-11, may be at least partially inserted through the incision 400 and used to retract the subcutaneous tissue. Electrocautery dissection, which may utilize an electrocautery device 304 in conjunction with the electrocautery guide 300 shown and described above with reference to FIG. 10, and/or blunt dissection, which may utilize a "hockey stick" type dissector as is known in the art, may be performed through the body tissues down to the level of the pectoralis major muscle. Subsequently, the pectoralis major muscle can be dissected to elevate it off the chest wall and attached rib. This process creates a subpectoral pocket underneath the pectoralis major muscle for placement of the breast implant. Alternatively, the pocket could be created between the breast tissue and the pectoralis major muscle, such that placement of the implant would occur on top of the muscle rather than beneath it.

An endoscope, such as the standard 10 mm or 5 mm type described above, can be received in retractor 10, 110, 210 to aid in dissection of tissues within the pocket to the clavicle superiorly, the sternum medially, and the lateral border of the pectoralis major muscle. The inferior border of the pectoralis muscle may then be incised, such as with an electrocautery device 304, to fully release the muscle and expand the pocket. An electrocautery device 304 may also be used for coagulation of any bleeding vessels created during dissection of the pocket.

After creation of the pocket, an inflatable implant can be completely evacuated of air, rolled up tightly into a cigar-like shape, and introduced through the incision 400 into position within the pocket. Any FDA approved breast implant having the desired structure may be used in accordance with the present invention. As is known in the art, a fill tube of the implant can be inserted through a self-sealing implant valve, and the fill tube connected to a syringe or other device that fills the implant with sterile physiologic saline (or another fluid, such as silicone) to the desired volume.

The above procedure can be repeated for the opposite breast. Final adjustments of implant position may be made with the patient in a sitting position. At the conclusion of the surgery, the patient may be placed back in a supine position, the fill tubes taken out causing the implant valve to self-seal, and the incision 400 closed. According to one aspect of the present invention, the incision 400 may be closed in three layers. First, the breast tissue may be closed using absorbable suture. Second, the flaps of the incision 400 can be trimmed to resemble a diamond shape, and the dermis may be closed with a permanent suture, which may take tension off the skin and prevent the healing scar from stretching from the weight of the implant and gravity. Third, the skin can be closed using an absorbable suture. The scar resulting from the method of the present invention may be approximately 1 cm in length and hidden in the fold of the breast. Since the tension on the scar can be mostly taken up by the permanent suture, the resultant scar heals very well and with optional adjuvant therapy of a silicone based covering, is almost non-existent.

Although the method and instruments according to the present invention have been described herein for use in breast augmentation mammaplasty, specifically with respect to an inframammary crease incision, it is understood that the method and instruments could also be employed if alternative incision sites are selected for breast augmentation surgery. Furthermore, the method and instruments of the present invention could be utilized for other surgical procedures such as, but not limited to, face lifts, brow lifts, or other endoscopic surgeries.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An endoscopic retractor, comprising:
   a curved shaft;
   a tubular member connected to the shaft, the tubular member including a hollow endoscope guide portion formed integrally with a generally flattened blade portion, wherein the endoscope guide portion transitions into the blade portion such that an end of the blade extends beyond an end of the endoscope guide along a blade axis; and
   a secondary blade pivotably attached to the blade portion of the tubular member, the secondary blade having a closed position wherein a first end of the secondary blade is generally aligned with the blade axis and overlying an end of the blade portion, and the secondary blade having an open position wherein the first end is generally out of alignment with the blade axis and the blade portion end, thereby increasing an effective combined width of the first end and the blade portion end, the secondary blade including a generally arcuate second end having a securing mechanism comprising flanges sized to snap fit onto the tubular member for fixing the position of the secondary blade with respect to the tubular member.

2. The endoscopic retractor according to claim 1, further comprising a handle attached to the shaft.

3. The endoscopic retractor according to claim 1, wherein the blade extends about 2.0 cm beyond the endoscope guide end.

4. The endoscopic retractor according to claim 1, wherein the blade has a first width at the blade end, and the blade has a second width near the endoscope guide end, the first width being greater than the second width.

5. The endoscopic retractor according to claim 4, wherein the first width is between about 1.2 cm and 1.6 cm, and the second width is between about 0.8 cm and 1.2 cm.

6. The endoscopic retractor according to claim 4, wherein the first width is between about 1.4 to 1.8 times greater than a diameter of the guide portion.

7. The endoscopic retractor according to claim 1 further comprising a passage for at least one of suction and irrigation mounted to the shaft.

8. The endoscopic retractor according to claim 7, wherein the passage is arranged to extend through the tubular member.

9. The endoscopic retractor according to claim 1, wherein the endoscope guide end is constructed with an angle of about 30°.

10. The endoscopic retractor according to claim 1, wherein the retractor is constructed from a metallic material.

11. The endoscopic retractor according to claim 1, wherein the retractor is at least partially formed with an insulating material.

12. The endoscopic retractor according to claim 1, wherein the first end of the secondary blade has a width of between about 1.2 cm and 1.6 cm.

13. A method for performing breast augmentation mammaplasty in a patient, comprising:
    making an incision to gain access to an area underneath the breast of the patient;
    providing an endoscopic retractor including a curved shaft and a tubular member connected to the shaft, the tubular member including a hollow endoscope guide portion integrally formed with a generally flattened blade portion, wherein the endoscope guide portion transitions into the blade portion such that an end of the blade extends beyond an end of the endoscope guide along a blade axis, and a secondary blade pivotably attached to the blade portion of the tubular member, the secondary blade having a closed position wherein a first end of the secondary blade is generally aligned with the blade axis and overlying an end of the blade portion, and the secondary blade having an open position wherein the first end is generally out of alignment with the blade axis and the blade portion end, thereby increasing an effective combined width of the first end and the blade portion end, the secondary blade including a generally arcuate second end having a securing mechanism comprising flanges sized to snap fit onto the tubular member for fixing the position of the secondary blade with respect to the tubular member; and
    inserting the retractor at least partially through the incision to aid in placing a breast implant within the patient.

14. The method according to claim 13, wherein the incision is placed adjacent to the inframammary crease of the breast.

15. The method according to claim 13, wherein the incision includes a first segment and a second segment generally perpendicular to and generally centered along the first segment.

16. The method according to claim 15, wherein the first segment is between about 0.5 and 1.5 cm, and the second segment is between about 0.25 and 0.75 cm.

17. The method according to claim 13, further comprising positioning the secondary blade in the closed position for inserting the retractor, and positioning the secondary blade in the open position after inserting the retractor.

18. The method according to claim 17, further including fixing the secondary blade in the open position by engaging the securing mechanism with the tubular member.

19. The method according to claim 13, further comprising creating a subpectoral pocket to contain the breast implant.

20. The method according to claim 19, wherein creating the pocket includes dissecting tissues using an electrocautery device.

21. The method according to claim 13, further comprising inserting an inflatable implant through the incision, and filling the implant with a fluid to a desired volume.

22. The method according to claim 21, wherein the fluid includes one of saline and silicone.

23. The method according to claim 13, further comprising closing the incision in three layers by closing the breast tissue with an absorbable suture, closing the overlying dermis with a permanent suture, and then closing the overlying skin with an absorbable suture.

* * * * *

UNITED STATES PATENT AND TRADEMARK OFFICE
CERTIFICATE OF CORRECTION

| | | |
|---|---|---|
| PATENT NO. | : 7,951,077 B2 | Page 1 of 1 |
| APPLICATION NO. | : 11/182995 | |
| DATED | : May 31, 2011 | |
| INVENTOR(S) | : Ayoub Sayeg and John Nemazi | |

It is certified that error appears in the above-identified patent and that said Letters Patent is hereby corrected as shown below:

Title Page: Item 73

The Assignee section was omitted. Please add Dr. Ayoub Sayeg as the Assignee, West Bloomfield, Michigan.

Signed and Sealed this
Eighteenth Day of October, 2011

David J. Kappos
*Director of the United States Patent and Trademark Office*